(12) United States Patent
Körfer et al.

(10) Patent No.: US 11,939,281 B2
(45) Date of Patent: Mar. 26, 2024

(54) PROCESS FOR THE PURIFICATION OF HYDROGEN CYANIDE

(71) Applicant: Evonik Operations GmbH, Essen (DE)

(72) Inventors: Martin Körfer, Kahl (DE); Michael Eicker, Bergisch Gladbach (DE); Catrin Dorothee Becker, Frankfurt (DE); Thorsten Merker, Erftstadt (DE); Marko Bussmann, Bornheim (DE)

(73) Assignee: Evonik Operations GmbH, Essen (DE)

( * ) Notice: Subject to any disclaimer, the term of this patent is extended or adjusted under 35 U.S.C. 154(b) by 739 days.

(21) Appl. No.: 17/256,861

(22) PCT Filed: Jul. 17, 2019

(86) PCT No.: PCT/EP2019/069235
§ 371 (c)(1),
(2) Date: Dec. 29, 2020

(87) PCT Pub. No.: WO2020/025322
PCT Pub. Date: Feb. 6, 2020

(65) Prior Publication Data
US 2021/0269396 A1    Sep. 2, 2021

(30) Foreign Application Priority Data
Jul. 30, 2018  (EP) .................................. 18186212

(51) Int. Cl.
*C07C 319/20* (2006.01)
*B01D 3/00* (2006.01)
*C01C 3/02* (2006.01)
*C07C 319/28* (2006.01)

(52) U.S. Cl.
CPC ............ *C07C 319/20* (2013.01); *B01D 3/007* (2013.01); *B01D 3/008* (2013.01); *C01C 3/0295* (2013.01); *C07C 319/28* (2013.01)

(58) Field of Classification Search
None
See application file for complete search history.

(56) References Cited

U.S. PATENT DOCUMENTS

| 2006/0201798 A1 | 9/2006 | Bartsch et al. |
| 2012/0215022 A1 | 8/2012 | Buss et al. |
| 2014/0213819 A1 | 7/2014 | Buss et al. |
| 2015/0197489 A1 | 7/2015 | Buss et al. |
| 2016/0167975 A1 | 6/2016 | Caton et al. |
| 2018/0194640 A1 | 7/2018 | Parten et al. |

FOREIGN PATENT DOCUMENTS

| CN | 1771197 A | 5/2006 |
| CN | 103347854 A | 10/2013 |
| CN | 106365178 A | 2/2017 |
| WO | WO 2004/092068 A1 | 10/2004 |
| WO | WO 2015/006548 A1 | 1/2015 |
| WO | WO 2015/142718 A1 | 9/2015 |
| WO | WO 2017/011428 A1 | 1/2017 |

OTHER PUBLICATIONS

International Search Report and Written Opinion dated Oct. 10, 2019 in PCT/EP2019/069235 filed Jul. 17, 2019.

*Primary Examiner* — Michael Barker
(74) *Attorney, Agent, or Firm* — Oblon, McClelland, Maier & Neustadt, L.L.P.

(57) ABSTRACT

The present invention relates to a process for the purification of hydrogen cyanide, comprising the steps of a) splitting a liquid feed stream (1) comprising hydrogen cyanide into at least a first liquid stream (2) and a second liquid stream (3), b) introducing the first liquid stream (2) into a distillation column (4) at a point between the top and the bottom of the distillation column, c) introducing the second liquid stream (3) into the distillation column (4) at the top of the distillation column, d) withdrawing an overhead vapor stream (5) enriched in hydrogen cyanide from the distillation column (4), and e) withdrawing a bottom stream (6) depleted in hydrogen cyanide, wherein the temperature of the second liquid stream (3) in step c) is lower than the temperature of the first liquid stream (2) in step b).

15 Claims, 3 Drawing Sheets

PROCESS FOR THE PURIFICATION OF HYDROGEN CYANIDE

FIELD OF THE INVENTION

The present invention relates to a process for the purification of hydrogen cyanide. Further, the present invention also relates to a process for the preparation of 2-hydroxy-4-(methylthio)butyronitrile by reacting the hydrogen cyanide obtained from the purification process according to the present invention with 3-mercaptopropionaldehyde.

BACKGROUND OF THE INVENTION

Hydrogen cyanide (HCN) can be prepared either in the so-called Andrussow process or in the so-called BMA process or Degussa process. The Andrussow process gives hydrogen cyanide in a gas phase reaction from methane, ammonia, and oxygen in the presence of a platinum catalyst:

$$CH_4+NH_3+1.5O_2 \rightarrow HCN+3H_2O, \Delta H_R=-481.06 \text{ kJ/mol}$$

Ammonia, natural gas (methane) and oxygen are fed into a reactor and react in the presence of a platinum catalyst at a temperature in the range of from 800 to 1500° C. Typically, the methane is supplied from natural gas, which can be further purified; $C_2$, $C_3$, and higher hydrocarbons (e.g., ethane, ethene, propane, propene, butane, butene, isobutene, etc., collectively termed $C_2+$ hydrocarbons) can be present in natural gas. While air can be used as a source of oxygen, the reaction can also be carried out using undiluted oxygen or oxygen-enriched air (i.e., in an oxygen Andrussow process). The reaction heat provided by the main reaction leads to a multitude of side reactions, which are further discussed in detail in the literature, e.g. in Waletzko, N., Schmidt, L. D. "Modeling Catalytic Gauze Reactors: HCN Synthesis", AIChE Journal vol. 34, no. 7, 1146-1156 (1988).

In the Andrussow process, the primary reactor output therefore includes hydrogen cyanide, unreacted ammonia, carbon monoxide, nitrogen and further reaction by-products, in particular nitriles, such as acetonitrile, acrylonitrile and propionitrile.

The name BMA process is abbreviated from Blausäure (hydrogen cyanide) from Methan (methane) and Ammoniak (ammonia) in German. Accordingly, the name BMA already indicates that this process is for the production of hydrogen cyanide from methane and ammonia in the presence of a platinum catalyst. The reaction equation is analog to the steam methane reforming (SMR) reaction of methane and water:

$$CH_4+NH_3 \rightarrow HCN+3H_2, \Delta H_R=251 \text{ kJ/mol}$$

The reaction is extremely endothermic and the reactants methane and ammonia are reacted in an alumina tube coated with a platinum catalyst at approximately 1400° C. The thus obtained product mixture contains about 23 vol.-% hydrogen cyanide and about 72 vol.-% of hydrogen as well as minor quantities of ammonia.

In both processes, the product gas stream containing hydrogen cyanide and un-reacted ammonia is quenched to temperatures of about 100 to 400° C. at the outlet. Subsequently, the thus cooled product stream is sent to an ammonia removal process, in which the ammonia is converted to a non-volatile ammonium salt by contacting the ammonia with an aqueous acidic solution, e.g. phosphoric acid or sulfuric acid. Next, the ammonia-free product gas stream is sent to an HCN absorption column, where HCN is absorbed in water. The thus obtained aqueous HCN solution is then purified in a distillation column to give a hydrogen cyanide containing overhead stream and an aqueous bottom stream, which can be either recycled or disposed of. In detail, the aqueous HCN solution is purified in a standard distillation column, into which it is introduced at a single point between the top and the bottom of a distillation column, the so-called feed stage. This point of introduction or feed stage also subdivides the distillation column into a rectifying section above the feed stage and a stripping section below the feed stage. In the processes of the prior art, the vapor reaching the top of the column is cooled and condensed to liquid in the overhead condenser, which may be placed either inside the top of the distillation column or outside of the distillation column (see for example, the overview article Cyano Compounds, Inorganic in Ullmann's Encyclopedia of Industrial Chemistry, Wiley-VCH Verlag GmbH & Co. KGaA, Weinheim, 2012, Vol. 10, pages 673 to 710, in particular chapter 1.2, pages 675 to 678 and FIG. 3 on page 676). Part of this liquid is returned to the column as reflux and the remainder is withdrawn as distillate, or overhead product. This overall flow pattern in a distillation column provides countercurrent contacting of ascending vapor and liquid streams, running down the packing(s) or the trays, on all of the packing(s) or trays throughout the column. However, the reflux, which is required to achieve a desired purity of hydrogen cyanide, leads to an accumulation of higher nitriles, e.g. acetonitrile, acrylonitrile and propionitrile within the column. When said nitriles are present in high concentrations, two separate liquid phases can occur inside the column, which leads to the problem of polymerization, which typically takes place at the phase boundary between the two liquid phases, and to foam formation.

The published patent application WO 2017/011428 A1 discloses a process for reducing the amounts of nitriles in hydrogen cyanide. Specifically, this document teaches a process that includes feeding a reaction product including HCN, water and nitriles to a separation vessel, taking a liquid slip stream comprising HCN, water and nitriles from the separation vessel, and feeding the liquid slipstream into a side stream stripper to purge nitriles from the HCN comprising mixture. However, the experimental data of WO 2017/011428 A1 show that this process does not suppress or at least significantly reduce the accumulation of nitriles in the separation vessel. Rather, the nitriles purge stream leaving the sidestream stripper contains considerable amounts of nitriles.

Thus, there was still a need for a method, which suppresses the accumulation of nitriles and also the formation of polymeric by-products in the purification of hydrogen cyanide, such as it is obtained from the Andrussow or BMA process.

SUMMARY OF THE INVENTION

It was found that this problem is solved in that the overhead vapor stream enriched in hydrogen cyanide, which is withdrawn from a distillation column, is not liquefied in a condenser or external heat exchanger, as in standard distillation processes. Accordingly, there is no external reflux of a liquefied overhead stream back to the top of the distillation column. Rather, the hydrogen cyanide containing feed stream is fed to a special distillation process, which in contrast to standard distillation processes involves the splitting of the hydrogen cyanide containing liquid feed stream (1) into at least two streams (2) and (3). The stream (2) is introduced into the distillation column at a point between the top and the bottom of the distillation column. In addition to said stream (2), an optional further stream, also split from the feed stream (1), can be introduced into the distillation column at a point between the top and the bottom of the distillation column, which is different from the point of introduction of stream (2). The stream (3) is introduced into the distillation column at the top of said distillation column. In order to provide for reflux, which is necessary to achieve the separation of components in the column, in particular with a specific degree of purification, stream (3) is introduced into the distillation column at a temperature lower than the temperature of stream (2) and the optional further stream. A bottom stream depleted in hydrogen cyanide is withdrawn from the bottom of the distillation column, and an overhead vapor stream enriched in hydrogen cyanide is withdrawn from the distillation column.

An object of the present invention is therefore a process for the purification of hydrogen cyanide, comprising the steps of
  a) splitting a liquid feed stream (1) comprising hydrogen cyanide into at least a first liquid stream (2) and a second liquid stream (3),
  b) introducing the first liquid stream (2) with a temperature T1 into a distillation column (4) at a point between the top and the bottom of the distillation column,
  c) introducing the second liquid stream (3) with a temperature T2 into the distillation column (4) at the top of the distillation column,
  d) withdrawing an overhead vapor stream (5) enriched in hydrogen cyanide from the distillation column (4), and
  e) withdrawing a bottom stream (6) depleted in hydrogen cyanide from the distillation column (4),
wherein the temperature T2 of the second liquid stream (3) in step c) is lower than the temperature T1 of the first liquid stream (2) in step b).

DETAILED DESCRIPTION OF THE INVENTION

Figure 1:
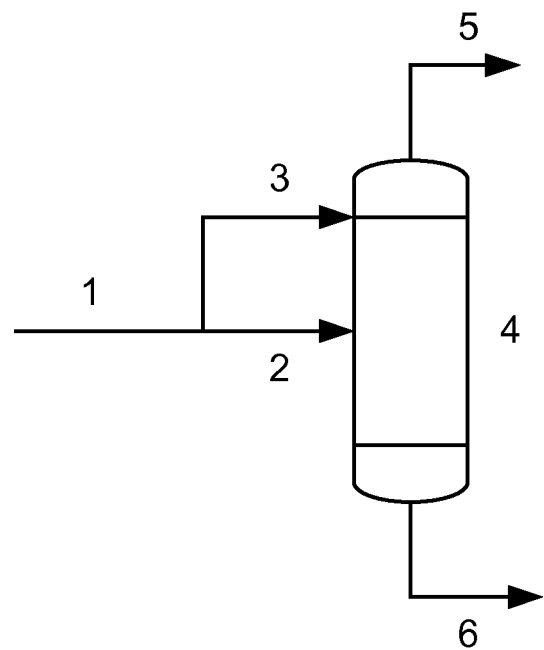
FIG. 1 is a schematic representation of a process for the purification of hydrogen cyanide according to the present invention.

The distillation column used in the process according to the present invention comprises at least one boiler or reboiler, which provides the energy required for evaporating the components in the distillation column.

In distillation column used in the purification process according to the present invention is not limited to a specific type of distillation column and may be a tray column, a randomly packed column, or a column with a structured packing.

The liquid feed stream (1) of step a) can be obtained from an HCN absorption column, where HCN is absorbed in water. In this case, the liquid feed stream (1) of step a) is an aqueous hydrogen cyanide comprising stream which preferably comprises a combined amount of water and hydrogen cyanide of at least 90% by weight, more preferably at least 98% by weight. The same then applies to the first and second liquid streams (2) and (3) as well as any optional further stream, which is also split from the liquid feed stream (1) comprising hydrogen cyanide. The process according to the present invention is not limited regarding the concentration of specific components, in particular hydrogen cyanide, in this liquid feed stream (1). The same necessarily applies to the first and second liquid streams (2) and (3) and any further stream, split from said feed stream (1). Therefore, the liquid feed stream (1) can contain from 1 to 99 wt.-% of hydrogen cyanide, preferably from 1 to 75 wt.-%, from 1 to 50 wt.-%, from 1 to 25 wt.-% of hydrogen cyanide. In particular, the liquid feed stream (1) comprises from 1 to 7 wt.-% of hydrogen cyanide, very particularly from 4 to 5 wt.-% of hydrogen cyanide. Typically, the content of nitriles strongly depends on the composition of the feed stream comprising natural gas, fed into the hydrogen cyanide reactor. Preferably, the combined amount of acetonitrile and acrylonitrile in liquid feed stream (1) is in the range of from 1 to 5000 ppm by weight.

It was found that the purification process according to the present invention leads to a significant reduction in the accumulation of nitriles and polymeric by-products inside the distillation column. In particular, it was found that the accumulation of acetonitrile and acrylonitrile is significantly reduced in the process according to the present invention. Specifically, the amount of by-products acetonitrile and acrylonitrile is close to zero at each tray of a tray distillation column used in the process according to the present invention. By comparison, by-products acetonitrile and acrylonitrile can accumulate to almost 60% at the top of the distillation column in a prior art distillation process for purifying crude hydrogen cyanide. Without wishing to be bound to a specific theory, it is believed that this effect is based on the different temperature profile along the distillation column in the process according to the present invention, compared to the temperature profile along the distillation column in a prior art distillation process for purifying hydrogen cyanide. A temperature of about 26° C. is measured at the top of a prior art distillation column when a crude hydrogen cyanide is distilled with a reflux ratio of 1. Higher nitriles, such as acetonitrile and acrylonitrile, have boiling points between the boiling points of HCN and water. Therefore, these by-products typically accumulate within the distillation column. However, any accumulation of nitriles within the column inevitably favors the formation of two liquid separate phases. Even more problematic is the formation of polymeric by-products, which takes place at the phase boundary between the phases. Accordingly, said phase separation favors polymerization, which inevitably leads to fouling inside the distillation apparatus and may require shut-down of the distillation. Compared to prior art distillation processes, the process according to the present invention leads to higher temperatures at the top of the distillation column. Specifically, temperatures of more than 30° C. are measured at the top of the distillation column (4) in the process according to the present invention. These higher temperatures at the top of the distillation column of the process according to the present invention lead to higher amounts of water at the top of the distillation column, compared to prior art processes. This prevents phase separation in the distillation column of the process according to the present invention as well as the accumulation of by-products, such as acetonitrile and acrylonitrile, in a separate liquid phase.

In addition, the process according to present invention also leads to significant savings in the energy input for the operation of the distillation column (4), compared to a prior art process for the purification of hydrogen cyanide. Specifically, it was found that the process according to present invention reduces the reboiler duty of the distillation column (4) by more than 20%, compared to a prior art distillation process for the purification of hydrogen cyanide.

In order to avoid any phase separation during the purification of liquid streams comprising hydrogen cyanide, the distillation column (4) is preferably operated at a temperature of at least 30° C., preferably at least 35, 40, or 45° C. at the column top.

In an embodiment of the process according to the present invention the distillation column (4) is operated at a temperature of at least 30° C. at the column top.

In a preferred embodiment of the process according to the present invention the distillation column (4) is operated with a temperature in the range of from 30° C. to 50° C. at the column top.

In particular, the distillation column (4) is operated at a temperature in the range of from 35° C. to 50° C., 40° C. to 50° C. or 45° C. to 50° C. at the column top.

The splitting of the feed stream (1) also allows an adjustment of the fractions of each of the streams (2) and (3) as well as of any other stream in addition to streams (2) and (3). The chosen flow rates of the thus obtained streams (2), (3) and any optional further streams in addition to stream (2) correspond to the desired fraction for these streams. The total of the streams (2) and (3) as well as of any stream in addition to stream (2) equals the input flow of the feed stream (1). Hence, the splitting of the feed stream (1) also allows to adjust a specific mass flow ratio or fraction of the first liquid stream (2) to the second liquid stream (3).

It was found that a mass flow ratio of the first liquid stream (2) to the second liquid stream (3) in the range of from 95:5 to 50:50 is not only suitable to suppress the accumulation of nitriles and the formation of polymeric by-products in the distillation column (4), but also saves all or at least part of the cooling required for condensing the vapor reaching the top of the distillation column and the energy required for evaporating the condensed vapor, which is fed back to the distillation column as reflux. Already a small stream (3), relative to the stream (2) is sufficient to achieve a purification of hydrogen cyanide with a degree of quality comparable to a prior art procedure. In the process according to the present invention, the mass flow ratio of first liquid stream (2) to second liquid stream (3) preferably ranges from 95:5 to 50:50, from 90:10 to 50:50, from 85:15 to 50:50, from 80:20 to 50:50, from 75:25 to 50:50, from 70:30 to 50:50, from 65:35 to 50:50, from 60:40 to 50:50 or from 55:45 to 50:50. By decreasing the mass flow ratio of stream (2) to stream (3) from 85:15 to 75:25 the reboiler duty of the distillation column is decreased by more than 8%. At the same time the water content in the overhead vapor stream decreases from 13.9 wt.-% to 6.9 wt.-%. Further, a mass flow ratio of stream (2) to stream (3) with at least 50% of stream (2) reduces the maximum concentration of nitriles in the liquid phase within the distillation column from more than 56% in a prior art distillation process for purifying hydrogen cyanide to values of less than 1%. Thus, the accumulation of nitriles is significantly reduced.

In an embodiment of the process according to the present invention the mass flow ratio of the stream first liquid stream (2) to the second liquid steam (3) ranges from 95:5 to 50:50.

When the process according to the present invention involves the introduction of a further stream into the distillation column (4) in addition to the first liquid stream (2), the figures mentioned above and below for the mass flow of first liquid stream (2) correspond to the sum of the mass flow of the first liquid stream (2) and of said further stream in addition to stream (2).

A mass flow ratio of the first liquid stream (2) to the second liquid steam (3) in the range of from 90:10 to 75:25 has several benefits at once: First, it gives an overhead vapor stream with a water content of less than 7 wt.-%, which is acceptable for the further processing of hydrogen cyanide in large-scale processes. Second, a temperature of about 47° C. is measured at the top of the distillation column (4). This condition suppresses the accumulation of nitriles, and also suppresses the formation of polymeric by-products in the distillation column (4). Further, the energy consumption of the reboiler of the distillation column (4) decreases by a factor of 5%, compared to a prior art distillation process.

In a preferred embodiment of the process according to the present invention the mass flow ratio of the first liquid stream (2) to the second liquid steam (3) ranges from 90:10 to 70:30.

Without wishing to be bound to a specific theory, it is believed that the savings in reboiler duty result from the decreased mass flow of the first liquid stream (2), compared to a prior art distillation process. The lower mass flow of the stream (2) therefore can be heated up to higher temperatures than the complete feed stream of a prior art distillation procedure, which leads to a smaller energy consumption than in a prior art distillation procedure.

One could speculate that a similar reduction in energy consumption would occur in prior art distillation procedure, when the reflux ratio is reduced. However, simulation results demonstrate that reducing the reflux ratio in a prior art distillation of crude HCN to a value of ca. 0.26 provides no savings in steam or chilled water. By comparison, purifying HCN to the same product quality in the process according to present invention, does not only save the complete chilled water, which is needed in the prior art process for the purification of hydrogen cyanide, but also saves more than 20% of steam. Chilled water must be produced in an energy intensive and expensive way. Thus, the process according to the present invention leads to overall energy savings of more than 34% compared to a prior art purification of HCN which gives the same product quality.

According to the present invention, the reflux, which is required to achieve a desired degree of purification, is provided by introduction of second liquid stream (3), which was split from the feed stream (1). In contrast to a standard distillation procedure for purifying HCN, the second liquid stream (3) is not heated prior to its introduction into the distillation column (4). Rather, said stream (3) is introduced into the distillation column (4) with a temperature, which is preferably lower than the head temperature of the distillation column in the process according to the present invention. Preferably, the temperature of the second liquid stream (3) in step c) is less than 30° C., less than 25° C., 20° C. at the most, 15° C. at the most, or 10° C. at the most. Preferably, the temperature of the second liquid stream (3) in step c) is in the range from 5° C. to less than 30° C., from 5° C. to less than 25° C., from 5° C. to 20° C. at the most, from 5° C. to 15° C. at the most, or from 5° C. to 10° C. at the most.

In another embodiment of the process according to the present invention the temperature T2 of the second liquid stream (3) in step c) is less than 25° C.

In a further embodiment of the process according to the present invention the first liquid stream (2) is heated prior to its introduction into the distillation column (4).

The thus heated stream (2) is then introduced as heated stream (8) into the distillation column (4).

In a preferred embodiment of the process according to the present invention the first liquid stream (2) is heated to a temperature T1 of from 25° C. to 130° C. at the most. The range of from 25° C. to 130° C. at the most comprises all conditions for performing the process according to the present invention, comprising a ratio of 50:50 of stream (2) to stream (3), an entirely liquid heated stream (8) and a bottom stream with pure water, with the lowest heat capacity. Preferably, the first liquid stream (2) is heated to a temperature T1 of from 25° C. to 95° C. at the most. This temperature T1 is particularly suitable for a mass flow ratio of stream (2) to stream (3) of 75:25, as shown in the example.

It is preferred that in the process according to the present invention the temperature T3 of the stream second liquid (3) in step c) is less than 25° C. and the temperature T1 of the first liquid stream (2) in step b) ranges from 25° C. to 130° C. at the most.

For an optimized heat integration, it is preferred to heat the first liquid stream (2) by heat exchange with the bottom stream (6) from the distillation column (4). Said bottom stream has a high heat capacity and therefore can transfer the most heat to the stream (2). This heating can be done in a heat exchanger (7). After transfer of heat from the bottom stream (6) to the stream (2), the thus heated stream (8) is introduced into the distillation column (4) and the thus cooled bottom stream (6) is either discarded or sent to a further utilization as stream (11). Said stream (11) mainly contains water and at most only a few ppm of high boiling by-products from the distillation. However, the extremely low amount of these by-products does not have any impact on the hydrogen cyanide. It is therefore preferred to send the stream (11) to an absorption tower in the preparation of hydrogen cyanide, in which the hydrogen cyanide is absorbed in water.

In yet another embodiment of the process according to the present invention, the first liquid stream (2) is heated by heat exchange with the bottom stream (6) from the distillation column (4).

A cooling of the second liquid stream (3) prior to its introduction into the distillation column (4) leads to a further improvement regarding the degree of purity of hydrogen cyanide. Said cooling can be performed by means of the heat exchanger (9), and the thus cooled stream (3) is introduced into the distillation column (4) as stream (10).

Preferably, the second liquid stream (3) is cooled prior to its introduction into the distillation column (4).

It is further preferred that the second liquid stream (3) is cooled to a temperature T2 between 5 and 20° C. prior to its introduction into the distillation column (4).

According to the present invention the first liquid stream (2) is introduced at a point between the top and the bottom of the distillation column (4). This particular point is often also referred to as feed stage, which subdivides the distillation column into a stripping section below the feed stage and a rectifying section above the feed stage. The feed stage is preferably chosen to provide from 30 to 70%, preferably from 50 to 65%, of the separation stages of the distillation column (4) in the stripping section and the remainder in the rectifying section. For example, when a distillation column has 20 separation stages, with the first stage at the top of the column and the 20th stage at the bottom, the feed stage is between the 6th to 14th of said 20 separation stages, preferably between the 7th to 10th of said 20 separation stages.

However, the process according to the present invention is not subject to any limitations regarding the number of streams into which the feed stream (1) is split and which are introduced into the distillation column. Hence, the process according to the present invention is also not subject to any limitations regarding the number of further streams in addition to first liquid stream (2), which are also introduced at a point along the distillation column. When the feed stream (1) is split into more than two streams, the one or more streams in addition to first liquid stream (2) is/are preferably introduced at a point along the rectifying section of the distillation column, which is different from the point of introduction of the first liquid stream (2). Preferably, this further stream in addition to first liquid stream (2) is introduced at a point between the top and the bottom of the distillation column (4), which is different from the introduction point of first liquid stream (2), in particular at a point between the points of introduction of the first and second liquid streams (2) and (3). It is further preferred, that said further stream is introduced into the distillation column with a temperature T3 that is between the temperature T1 of first liquid stream (2) upon introduction into the distillation column and the temperature T2 of second liquid stream (3) upon introduction into the distillation column.

In an embodiment the purification process according to the present invention further comprises the step of f) introducing at least one further liquid stream, which is also split from the liquid feed stream (1) comprising hydrogen cyanide, in addition to stream first liquid (2) into the distillation column (4) at a point between the points of introduction of the first and second liquid streams (2) and (3), wherein the temperature T3 of the further stream is between the temperature T2 of the second liquid stream (3) in step c) and the temperature T1 of the first liquid stream (2) in step b).

In a preferred embodiment of the purification process according to the present invention, the mass flow of the first liquid stream (2) which is introduced into the distillation column in step b) is larger than the mass flow of the at least one further stream, which is introduced into said distillation column in addition to first liquid stream (2).

In principle, the process according to the present invention aims at avoiding condensing a part or all of the overhead vapor stream (5) enriched in hydrogen cyanide and the feeding of the thus liquefied stream reflux to the top of the distillation column (4). Thus, in step d) said overhead vapor stream (5) enriched in hydrogen cyanide is preferably not condensed after being withdrawn from the distillation column (4). Accordingly, said overhead vapor stream (5) is preferably further processed without any condensation after being withdrawn from the distillation column (4).

Nevertheless, at least a part of the overhead vapor stream (5), after being withdrawn from the distillation column (4), may alternatively be condensed to give a liquefied stream (13), which is fed either to a further processing or to a storage tank. When the overhead vapor stream (5) is not completely condensed, the non-condensed part of the overhead vapor stream (5) makes up the residual vapor stream (14). The (partial) condensation of the overhead vapor stream (5) is performed in a condenser (12). This condensation does not have any impact on the purification process according to the present invention and the thus achieved beneficial effects, no matter how much of the overhead vapor stream is condensed after being withdrawn from the distillation column. Rather, this embodiment allows to react on fluctuations in the consumption of the hydrogen cyanide obtained from the process according to the present invention or to provide hydrogen cyanide in the required amounts and in a better transportable form for a customer. Therefore, this particular embodiment is not limited to any specific ratio of liquefied stream (13) to residual vapor stream (14).

In an alternative embodiment the purification process according to the present invention further comprises the steps of
  g) condensing at least a part of the overhead vapor stream (5) withdrawn from the distillation column (4) to give a liquefied stream (13) and, if applicable, a residual vapor stream (14), and
  h) feeding the liquefied stream (13) of step g) to a further processing or to a storage tank.

When the overhead vapor stream (5) is not completely condensed in step g), the non-condensed part of the overhead vapor stream (5), which makes up the residual vapor stream (14), is preferably fed directly, i.e. without any condensation, to a further processing. Alternatively, the overhead vapor stream (5) can be completely condensed in step g) to give a liquefied stream (13), which is fed to a further processing or to a storage tank in step h).

According to the process of the present invention, the hydrogen cyanide enriched overhead vapor stream (5) and/or the hydrogen cyanide enriched residual vapor stream (14) is/are not liquefied and can therefore be sent to a further processing in the vapor form in which they were obtained from the distillation. Therefore, the further processing of the overhead vapor stream (5) or the residual vapor stream (14) does not involve any storage of the streams. Rather, any of these streams is further processed directly, i.e. as obtained from the purification process according to the present invention, to a give a new chemical product or a mixture with the hydrogen cyanide.

In one embodiment of the purification process according to the present invention the overhead vapor stream (5) withdrawn from the distillation column (4) in step d) is further processed without condensation of said overhead vapor stream.

In another embodiment of the purification process according to the present invention the residual vapor stream (14) of step h) is further processed without condensation of said vapor stream.

In the context of the present invention, a further processing is any treatment of the overhead vapor stream (5) and/or residual vapor stream (14), in which any of said streams is either further reacted and/or mixed with any further components, with the exception of a liquefaction of any of said stream as such.

A further improvement regarding safety aspects is achieved when the overhead vapor stream (5) or the residual vapor stream (14), both enriched in hydrogen cyanide and obtained by the purification process according to the present invention, is converted into a less hazardous compound. This reduces the risk potential of hydrogen cyanide significantly. From an economic point of view, the thus obtained hydrogen cyanide derived compound should be a relevant final or intermediate product. In case of an intermediate product, said hydrogen cyanide derived compound should be easily convertible into other compounds of economic relevance.

Hydrogen cyanide is an important starting compound in the large-scale production of the essential amino acid D,L-methionine and in this process hydrogen cyanide is reacted with 3-methylthiopropanal, also known as 3-methylmercaptopropionaldehyde or under its abbreviation MMP, to give 2-hydroxy-4-methylthiobutytic acid nitrile. This reaction may be performed in the presence of suitable catalysts such as pyridine or trimethylamine. The thus obtained 2-hydroxy-4-methylthiobutytic acid nitrile can be hydrolyzed in the presence of mineral acid to give 2-hydroxy-4-methyl butyric acid, also known as methionine hydroxy analogue or under its abbreviation MHA. Alternatively, the 2-hydroxy-4-methylthiobutytic acid nitrile is further reacted with ammonium hydrogen carbonate to give the corresponding hydantoin, which is saponified with a base to give a methionate containing solution, from which the neutral methionine is precipitated by acidification of the solution with carbon dioxide or an acid. A further benefit of reacting hydrogen cyanide with 3-methylthiopropanal to 2-hydroxy-4-methylthiobutytic acid nitrile is that the latter compound has a much better storage stability than 3-methylthiopropanal. The preparation of 2-hydroxy-4-methylthiobutytic acid nitrile is disclosed for example in the published patent application US 2012/215022 A1. However, the process disclosed in this document involves the use of a crude product gas from the hydrogen cyanide production according to the Andrussow process, which therefore has a low content of hydrogen cyanide but a rather higher content of other components. However, these additional components do not contribute to any additional benefit in the preparation of 2-hydroxy-4-methylthiobutytic acid nitrile. Rather, they lead to very large substance stream, whose heating and conducting throughout the process requires a large apparatus design and a large energy input. This, however, makes the process of US 2012/215022 A1 rather unattractive from both an energy and an economic point of view. By comparison, the purification process according to the present invention allows to use hydrogen cyanide enriched vapor streams, i.e. the overhead vapor stream (5) or the residual vapor stream (14), in the preparation of 2-hydroxy-4-(methylthio)butyronitrile by reacting one of these streams with 3-methylmercaptopropionaldehyde. The process for the preparation of 2-hydroxy-4-(methylthio)butyronitrile according to the present invention therefore allows to give a 2-hydroxy-4-(methylthio)butyronitrile with a higher purity and less energy input than in the process of 2012/215022 A1.

Another object of the present invention is therefore a process for the preparation of 2-hydroxy-4-(methylthio)butyronitrile comprising the steps of
  i) purifying hydrogen cyanide in the process for the purification of hydrogen cyanide according to the present invention to provide an overhead vapor stream (5) enriched in hydrogen cyanide or a residual vapor stream (14) enriched in hydrogen cyanide, and
  ii) reacting said overhead vapor stream (5) enriched in hydrogen cyanide or said residual vapor stream (14) enriched in hydrogen cyanide with 3-mercaptopropionaldehyde to give 2-hydroxy-4-(methylthio)butyronitrile.

It is a further benefit of this process for the preparation of 2-hydroxy-4-(methylthio)butyronitrile that 3-mercaptopropionaldehyde, a compound which is susceptible to polymerization and degradation reactions, is converted into the storage stabile compound 2-hydroxy-4-(methylthio)butyronitrile.

As far as the step i) of this additional object is concerned, all of the aforementioned embodiments of the purification process according to the present invention apply.

EXAMPLES

Figure 2:
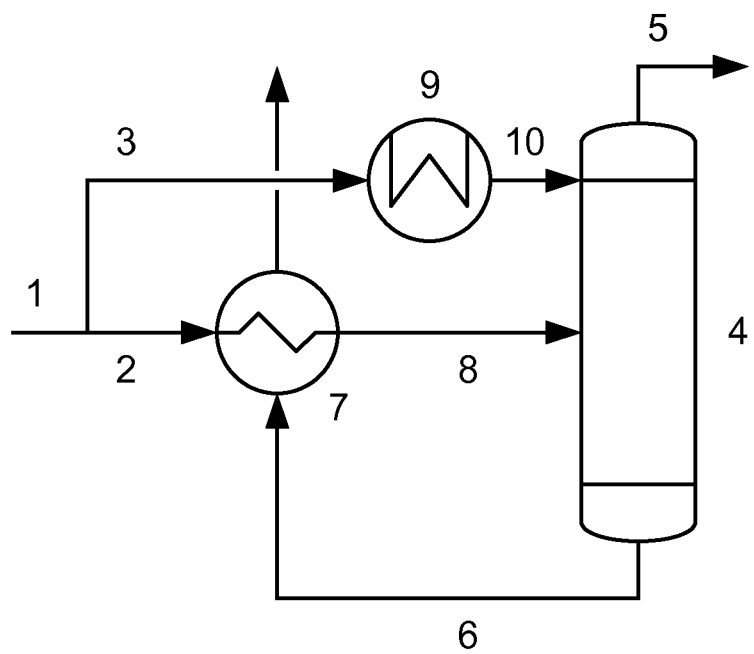
FIG. 2 shows an embodiment of the process of the invention where first liquid stream (2) is heated by heat exchange with bottoms stream (6) before it is introduced into distillation column (4).
Figure 3:
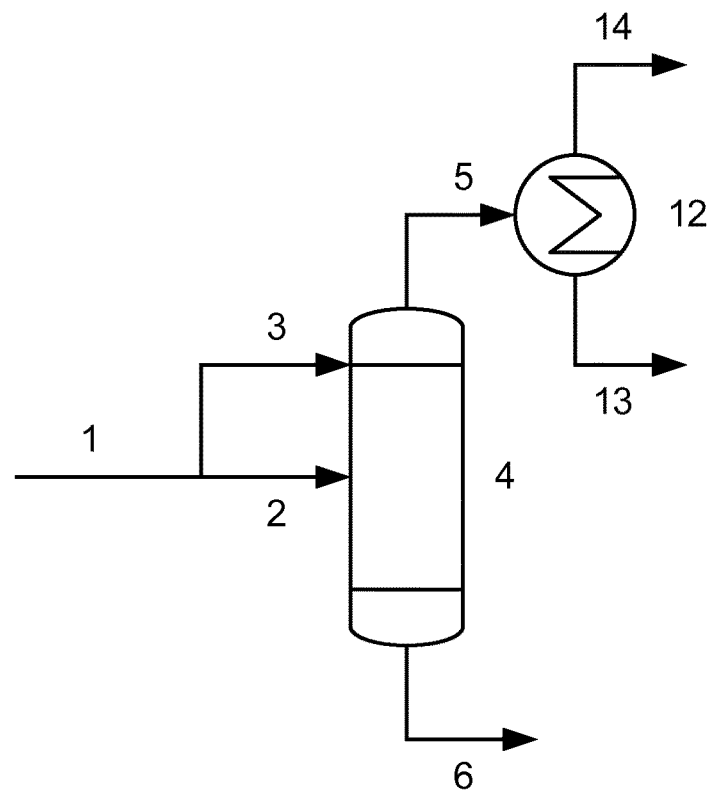
FIG. 3 shows an embodiment of the process of the invention where all or a part of overhead vapor stream (5) withdrawn from distillation column (4) is condensed to give a liquefied stream (13) and, if applicable, a residual vapor stream (14).
Figure 4:
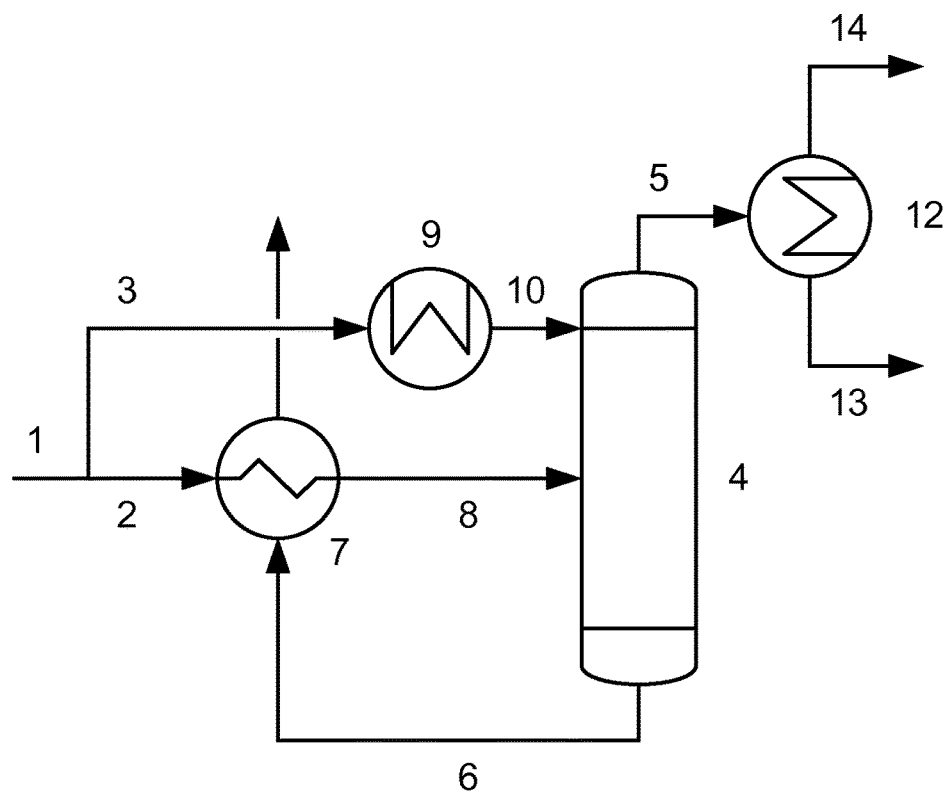
FIG. 4 shows an embodiment of the process of the invention combining the features shown in FIGS. 2 and 3.

The examples herein were performed using a computational model of a process based on the distillation process shown in FIG. 2. Process modelling is an established and reliable methodology used by engineers to simulate complex chemical processes before building the real plant. In the context of the examples herein the commercial modeling software Aspen Plus® (Aspen Technology, Inc., 20 Crosby Roads, Bedford, Mass. 01730, USA) was used in combination with physical property data available from public databases.

Example 1 Purification of a Hydrogen Cyanide Stream, Comprising Hydrogen Cyanide, According to the Invention Using the modeling software Aspen Plus®, the purification of the hydrogen cyanide comprising stream was simulated for the distillation process shown in FIG. 2: An aqueous feed stream (1) from an HCN absorption tower comprising 4 to 5% by weight hydrogen cyanide is split into a first liquid stream (2) and a second liquid stream (3). The stream (2) is heated to a temperature of 92° C. in the heat exchanger (7) by heat exchange with the bottom stream (6) from the distillation column (4) to give a heated stream (8). Said stream (8) is introduced between the 7th and 10th stage of a distillation column (4) having 20 stages. The thus obtained cooled bottom stream (11), which mainly comprises water, is recycled to the HCN absorption tower. The stream (3) is introduced at the top of the distillation column (4) with a temperature of 24.9° C. An overhead vapor stream (5) enriched in hydrogen cyanide is withdrawn from the top of the distillation column (4). A bottom stream (11), depleted in hydrogen cyanide and enriched in water, is withdrawn from the bottom of the distillation column and fed to the heat exchanger (7).

The water content in the overhead vapor stream (5), withdrawn from the distillation column (4), changes with the mass flow ratio of the first liquid stream (2) to the second liquid stream (3).

Figure 5:
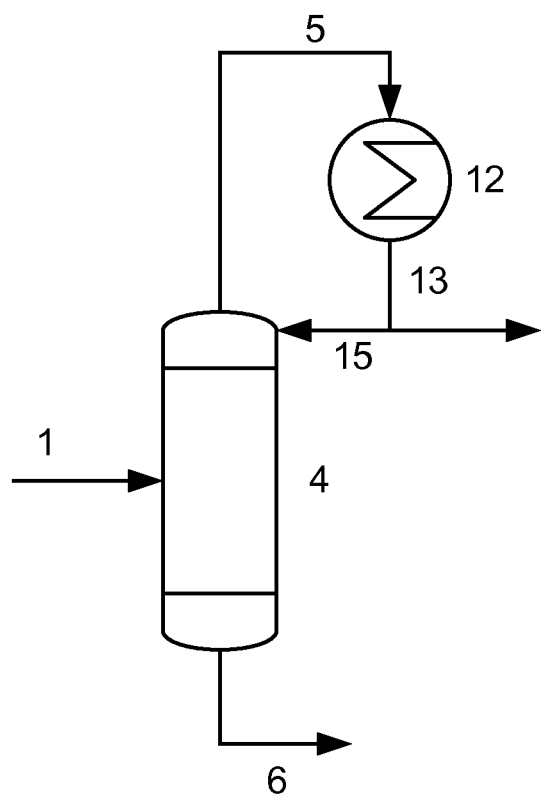
FIG. 5 shows a prior art process for the purification of hydrogen cyanide where the overhead vapor stream (5) withdrawn from distillation column (4) is condensed and a part of the resulting liquefied stream (13) is returned to distillation column (4) as reflux stream (15).

Specifically, the water content in the overhead vapor stream (5) is reduced from almost 14 wt.-% to less than 7 wt.-% by increasing the fraction of stream (3) from 15 to 25 wt.-%, i.e. by decreasing the mass flow ratio of stream (2) to stream (3) from 85:15 to 75:25. At the same time, the reboiler duty of the distillation column (4) decreases by almost 9%. A further increase of the fraction of the stream (3) to more than 25 wt.-% does not result in further reduction of the water content in the overhead vapor stream (5), nor does it result in a further reduction of the reboiler duty of the distillation column (4). Table 1 summarizes these results. In this table, prior art (last entry in Table 1) indicates the results calculated for a prior art distillation process for purifying hydrogen cyanide as shown in FIG. 5. In comparison to the process according to the prior art, the process according to the present invention gives a higher water content in the overhead vapor stream, which however is no problem at all for the further processing of the thus obtained hydrogen cyanide. More important than that is that the process according to the present invention leads to a tremendous reduction in the maximum accumulation of nitriles acetonitrile and acrylonitrile in the liquid phase (from more than 56 wt.-% to less than 0.1 wt.-%) and a significant reduction in the reboiler duty of the distillation column (from 7190 kW to 5700 kW).

TABLE 1

Influence of the split ratio of first liquid stream (2) to second liquid stream (3) on the water content in the overhead vapor stream (5) and on the reboiler duty of the distillation column (4).

| Mass flow ratio of stream (2) to stream (3) | Water content in overhead vapor stream (5) [wt.-%] | Reboiler duty of distillation column (4) [KW] | Max. accumulation of nitriles in liquid phase [wt.-%] |
|---|---|---|---|
| 85:15 | 13.9 | 6232 | 0.20% |
| 80:20 | 9.5 | 5892 | 0.10% |
| 75:25 | 6.9 | 5700 | 0.90% |
| 70:30 | 6.9 | 5700 | 0.60% |
| 65:35 | 6.9 | 5700 | 0.60% |
| 60:40 | 6.9 | 5700 | 0.60% |
| 55:45 | 6.9 | 5700 | 0.60% |
| 50:50 | 6.9 | 5700 | 0.60% |
| Standard: - | ~0% | 7190 | 56.40% |

A better heat integration leads to further improvements for the reboiler duty of the distillation column (4) in the process according to the present invention. In detail, the second liquid stream (3), which made up 25 wt.-% of the feed stream (1), is cooled to a temperature in the range of from 5 to almost 25° C., to give a cooled stream (10), which is introduced at the top of the distillation column (4). Further, the stream (2), which makes up 75 wt.-% of the stream (1), is heated to a temperature of 93° C., to give a heated stream (8), which is introduced at the feed stage of the distillation column (4). Said cooling leads to a further decrease of the water content in the overhead vapor stream (5) by 1.5 wt.-%. The higher cooling capacity of the cooler (9), which is required for the cooling of the second liquid stream (3), has to be compensated by the reboiler of the distillation column (4). Therefore, the reboiler duty in the distillation column (4) increases again, but only slightly (see table 2).

TABLE 2

Influence of the temperature of the stream (10) on the water content in the overhead vapor stream (5) and on the reboiler duty of the distillation column (4).

| Temperature of stream (10) [° C.] | Temperature of stream (8) [° C.] | Water content in overhead vapor stream (5) [wt.-%] | Reboiler duty of distillation column (4) [KW] |
|---|---|---|---|
| 10 | 93 | 5.4 | 6258 |
| 15 | 93 | 5.8 | 6069 |
| 20 | 93 | 6.3 | 5876 |
| 24.9 | 93 | 6.9 | 5700 |

Example 2 Comparison with a Prior Art Procedure

In this example, the result of purifying a hydrogen cyanide comprising stream in the prior art distillation process as shown in FIG. 5 (experimental data) is compared with the results of purifying a hydrogen cyanide comprising stream in the process according to the present invention (simulation data using Aspen Plus® for the process shown in FIG. 2). The prior art process was performed with a temperature of 47.3° C. at the top of the distillation column to give an overhead vapor stream (5) of the same composition and quality, in order to allow for a comparison of the operating parameters of the two processes. The same applies to the process according to the present invention. In the prior art distillation process, the temperature at the top of the distillation column was adjusted by a reflux ratio of 0.26. In the process according to the present invention, the temperature at the top of the distillation column (4) is adjusted by adjusting a fraction of 22.5 wt.-% for the second liquid stream (3). Further differences in the operation of the two distillation columns are avoided for a better comparison of the two processes. Therefore, the second liquid stream (3) is not heated before being introduced into the distillation column (4) in the process according to the present invention.

Compared to the prior art distillation process, the process according to the present invention has a significantly lower energy consumption for providing an overhead vapor stream of the same quality. In detail, there is not only a significant saving in chilled water, which otherwise has to be provided by a refrigeration machine, by omitting the reflux in the process according to the present invention, but there is also a big saving in steam. Table 3 summarizes these results.

TABLE 3

Comparison of the energy demand in a purification according to the prior art and a purification according to the invention at equal product qualities

| Process parameter | Purification according to the prior art | Purification according to the invention |
|---|---|---|
| Reflux ratio | 0.26 | — |
| Percentage of unheated feed stream | — | 22.5% |
| Resources | | |
| Chilled water [KW] | 1530 | 0 |
| Steam [KW] | 7190 | 5700 |
| Overhead vapor stream (5) | | |
| HCN [wt.-%] | 93.0 | 93.0 |
| H$_2$O [wt.-%] | 6.9 | 6.9 |
| T [° C.] | 47.3 | 47.3 |

This comparative example shows that it is not possible to compensate the lower cooling requirements and the lower steam consumption of the process according to the present invention by reducing the reflux ratio in the prior art process.

LIST OF REFERENCE SIGNS (1) liquid feed stream comprising hydrogen cyanide
(2) first liquid split stream to be introduced into the distillation column (4) at a point between the top and the bottom section of the distillation column (4)
(3) second liquid split stream to be introduced into the distillation column (4) at the top of the distillation column (4)
(4) distillation column
(5) overhead vapor stream enriched in hydrogen cyanide
(6) bottom stream depleted in hydrogen cyanide
(7) heat exchanger for heating first liquid stream (2)
(8) heated stream from the heat exchanger (7) to be introduced into the distillation column (4) at a point between the top and the bottom of the distillation column (4)
(9) heat exchanger for cooling second liquid stream (3)
(10) cooled stream from heat exchanger (9) to be introduced at the top of the distillation column (4)
(11) bottom stream from heat exchanger (7)
(12) (partial) condenser for overhead vapor stream (5)
(13) liquefied stream from (partial) condenser (12)
(14) residual vapor stream to be fed to further processing
(15) reflux stream from condenser (12)

The invention claimed is:

1. A process for the purification of hydrogen cyanide, comprising:
   a) splitting a liquid feed stream comprising hydrogen cyanide into at least a first liquid stream and a second liquid stream,
   b) introducing the first liquid stream with a temperature T1 into a distillation column at a point between the top and the bottom of the distillation column,
   c) introducing the second liquid stream with a temperature T2 into the distillation column at the top of the distillation column,
   d) withdrawing an overhead vapor stream enriched in hydrogen cyanide from the distillation column, and
   e) withdrawing a bottom stream (6) depleted in hydrogen cyanide from the distillation column,
   wherein the temperature T2 of the second liquid stream in step c) is lower than the temperature T1 of the first liquid stream in step b).

2. The process of claim 1, wherein the distillation column is operated with a temperature of at least 30° C. at the top of the distillation column.

3. The process of claim 1, wherein the distillation column is operated with a temperature in the range of from 30 to 50° C. at the top of the distillation column.

4. The process of claim 1, wherein the mass flow ratio of the first liquid stream to the second liquid stream ranges from 95:5 to 50:50.

5. The process of claim 1, wherein the mass flow ratio of the first liquid stream to the second liquid stream ranges from 90:10 to 70:30.

6. The process of claim 1, wherein the temperature T2 of the second liquid stream in step c) is less than 25° C.

7. The process of claim 1, wherein the first liquid stream is heated prior to its introduction into the distillation column.

8. The process of claim 7, wherein the first liquid stream is heated to a temperature T1 of from 25° C. to 130° C. at the most.

9. The process of claim 7, wherein the first liquid stream is heated by heat exchange with the bottom stream from the distillation column.

10. The process of claim 1, further comprising:
   f) introducing at least one further liquid stream, which is also split from the liquid feed stream comprising hydrogen cyanide, in addition to the first liquid stream and second liquid stream, into the distillation column at a point between the points of induction of the first and second liquid streams,
   wherein the temperature T3 of the at least one further stream is between the temperature T2 of the second liquid stream in step c) and the temperature T1 of the first liquid stream in step b).

11. The process of claim 10, wherein the first liquid stream is introduced into the distillation column in step b) at a larger mass flow rate than the at least one further stream, which is introduced into the distillation column in addition to the first liquid stream.

12. The process of claim 1, wherein the overhead vapor stream withdrawn from the distillation column in step d) is not condensed.

13. The process of claim 1, further comprising:
g) condensing at least a part of the overhead vapor stream withdrawn from the distillation column to give a liquefied stream and, optionally, a residual vapor stream, and
h) feeding the liquefied stream of step g) to a further processing or to a storage tank.

14. The process of claim 13, wherein the residual vapor stream of step h) is not condensed.

15. The process of claim 1, further comprising:
reacting the overhead vapor stream enriched in hydrogen cyanide with 3-mercaptopropionaldehyde to produce 2-hydroxy-4-(methylthio)butyronitrile.

* * * * *